United States Patent [19]

Blaney et al.

[11] Patent Number: 5,680,331
[45] Date of Patent: Oct. 21, 1997

[54] METHOD AND APPARATUS FOR MIMICKING PROTEIN ACTIVE SITES

[75] Inventors: Jeffrey M. Blaney; Michael A. Siani, both of Oakland, Calif.

[73] Assignee: Chiron Corporation, Emeryville, Calif.

[21] Appl. No.: 290,445

[22] Filed: Aug. 15, 1994

Related U.S. Application Data

[63] Continuation of Ser. No. 956,729, Oct. 5, 1992, abandoned.
[51] Int. Cl.[6] ........................................ G06G 7/48
[52] U.S. Cl. ............................... 364/578; 364/580
[58] Field of Search ..................... 530/326; 514/13; 364/578, 580

[56] References Cited

PUBLICATIONS

Rose *Adu Prot Chem* 37, 20–45 (185).

*Primary Examiner*—Paula K. Hutzell
*Assistant Examiner*—Benet Prickril
*Attorney, Agent, or Firm*—Richard Aron Osman; Kenneth M. Goldman; Robert P. Blackburn

[57] ABSTRACT

A method for generating multiple mimics of an active site of a molecule, such as a protein, using computer modeling of the active site. A putative active site is identified, and the amino acids, or residues, purportedly responsible for the biological activity in question are located. These are represented as virtual residues in a model of the active site. The method generates many different possible representations of the active site of the selected protein, presenting the user with a choice of premodeled molecules for synthesis and testing as a substitute for the protein.

19 Claims, 10 Drawing Sheets

METHOD AND APPARATUS FOR MIMICKING PROTEIN ACTIVE SITES

This is a continuation of application Ser. No. 07/956,729 filed 5 Oct. 1992, now abandoned.

BACKGROUND OF THE INVENTION

The present invention is directed to a method for mimicking active sites of molecules, in particular proteins, with particular application to the field of synthesizing small cyclic peptides.

It is well known that relatively confined regions of a protein are responsible for the biological activity of the protein, such as binding to a receptor or antibody. Considerable effort has been directed at generating peptides to complement invaginations or cavities at the receptor sites of proteins. For instance, many drugs are enzyme inhibitors; for a given protein enzyme, the standard approach has been to identify the active site of the protein, and then design a molecule which fits the active site, thereby "locking up" the protein and preventing a naturally occurring molecule from interacting with the site.

Standard research techniques are used to identify the active sites in proteins. The three-dimensional configurations of the molecules may be determined by any one of several known approaches, including: x-ray crystallography; nuclear magnetic resonance (NMR); or homology-based modeling, which is based upon modeling a protein by using a similar protein whose structure is well known, and which is the subject of a computer program called INSIGHTII, available from Bisoym Technologies, 10065 Barnes Canyon Road, San Diego, Calif., which is incorporated herein by reference as background relating to protein modeling.

This approach has certain useful applications, but little attention has been paid to the reverse problem, namely that of mimicking the proteins themselves, and to the advantages of doing so.

A given protein with a known biological effect may be produced in quantity with known methods, and provided to a patient for treatment. However, proteins do not make very successful drugs. They are metabolically unstable, for example, being easily destroyed by enzymes, and they are rarely fully absorbed by the body. Thus, the above type of treatment is less than satisfactory.

A substitute for treatment directly with proteins would therefore be of considerable value. To this end, the investigation of active sites of proteins can be applied to a different goal: that of actually mimicking the active sites by means of newly designed molecules. Such molecules should have a greater stability than the proteins for which they are to substitute, and should have effectively the same biological effects. It is the primary object of the present application to provide a method for generating such molecules.

SUMMARY OF THE INVENTION

The method of the invention thus involves identifying the putative active site of a molecule, determining the structure of the active site, and, by means of a depth-first recursive procedure, generating designs of molecules which mimic that site to a desired degree of accuracy. It is particularly applicable to proteins, but may be used to mimic active sites of other polymers.

Specifically, the invention provides a method for mapping a poly-Alanine of a predetermined length onto the backbone (i.e., the locations of the alpha carbons) of a protein's putative active site residues, by means Of the above-mentioned recursive procedure. The coordinates of the residues (which are amino acids) are located in three-dimensional space, and a template of the active site is generated. The template includes a residue corresponding to each of the residues of the active site. In addition, in order to complete a structure which is chemically feasible, an outline of the active site is generated, which includes dummy residues added to the template, such as where an interresidue distance is too great for a covalent bond to be achieved. Thus, the dummy residues do not correspond to alpha carbons of residues at the active site, but are provided for structural stability.

Many different possible mappings of mimics onto the template are considered. A given mimic may include sufficient residues (with alpha carbons) to have a one-to-one correspondence with the alpha carbons of the active site. Alternatively, there may be fewer residues in a given mimic than in the active site, in which case some of the alpha carbons of the residues of the active site will not be represented. In either of the above cases, the mimic may also include dummy residues.

Given the distance constraints between alpha carbons, all possible mappings onto the active site are systematically considered by the generation of virtual paths between the alpha carbons. A "virtual path" refers to a chemical path or structural element in the mimic which is not directly represented in the original protein.

The paths are generated beginning with a first residue, and then in a depth-first approach, considering each of the possible paths which result in mimics with alpha-carbons in the correct positions. A given path under consideration is rejected if the alpha-carbon-alpha-carbon distances found in the template cannot be achieved.

The length of the path, i.e. the number of residues which may be represented, is selected in advance, and generally will be equal to or less than the number of residues of the template.

Upon the generation of a valid path of the desired length, i.e. a mimic of the active site, it is then determined whether it is actually possible to construct such a molecule in three-dimensional space. Disulfide bonds may be introduced for structural stability and to constrain conformational flexibility, and the molecule design is subjected to simulated annealing for energy minimization. The lowest-energy conformers to the generated molecule which are consistent with the actual active site of the protein are selected for synthesis.

The method of the invention may conveniently be carried out with the assistance of a standard microcomputer or other computer, and the information necessary to generate the mimics is stored in memory in a conventional fashion.

DESCRIPTION OF THE PREFERRED EMBODIMENTS

Figure 2:
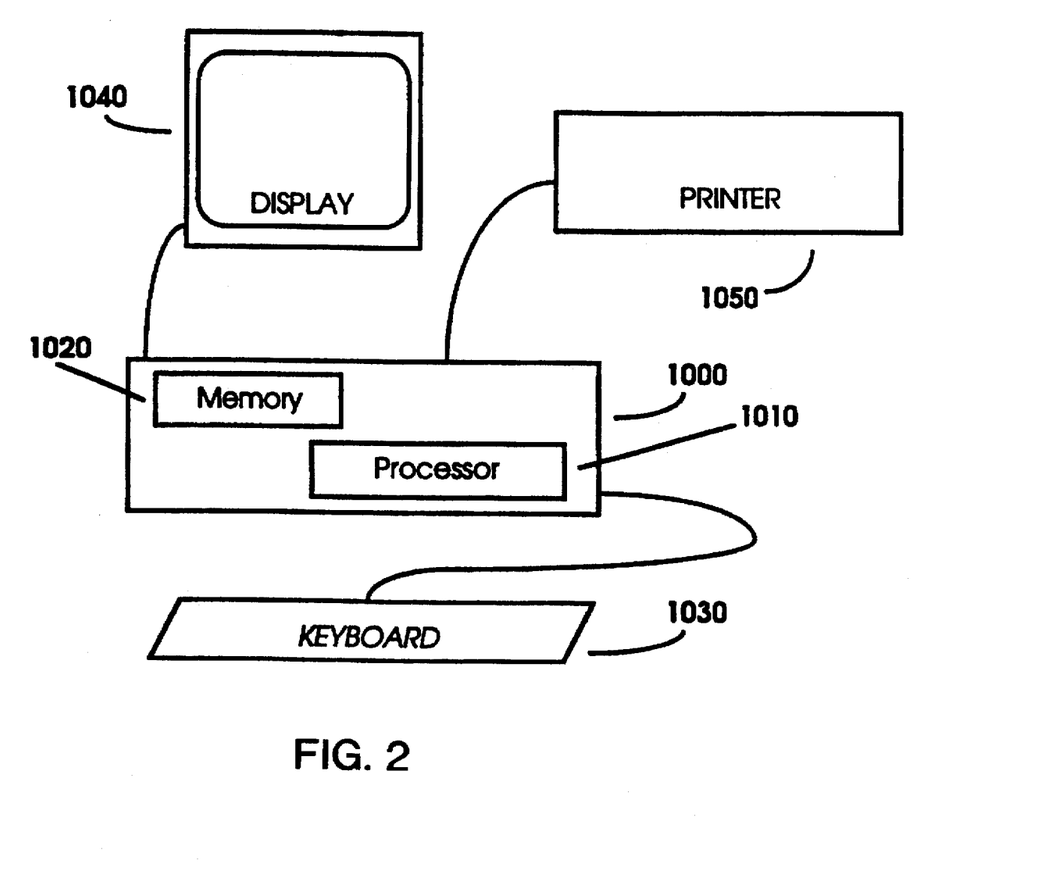
FIG. 2 is a block diagram of a computer system in connection with which the invention may be implemented.

The method of the invention for generating mimics of the active sites of proteins is preferably carried out with the use of a conventional computer 1000 as shown in FIG. 2, comprising a microprocessor 1010, a memory 1020, an input device 1030 such as a keyboard, and a display 1040, printer 1050, or other output device. Thus, programs may be generated which carry out the calculation steps of the invention described below, without undue effort. Many general purpose microcomputers with such standard configurations are available which are suitable for implementing steps of the invention as discussed below.

Figure 1A:
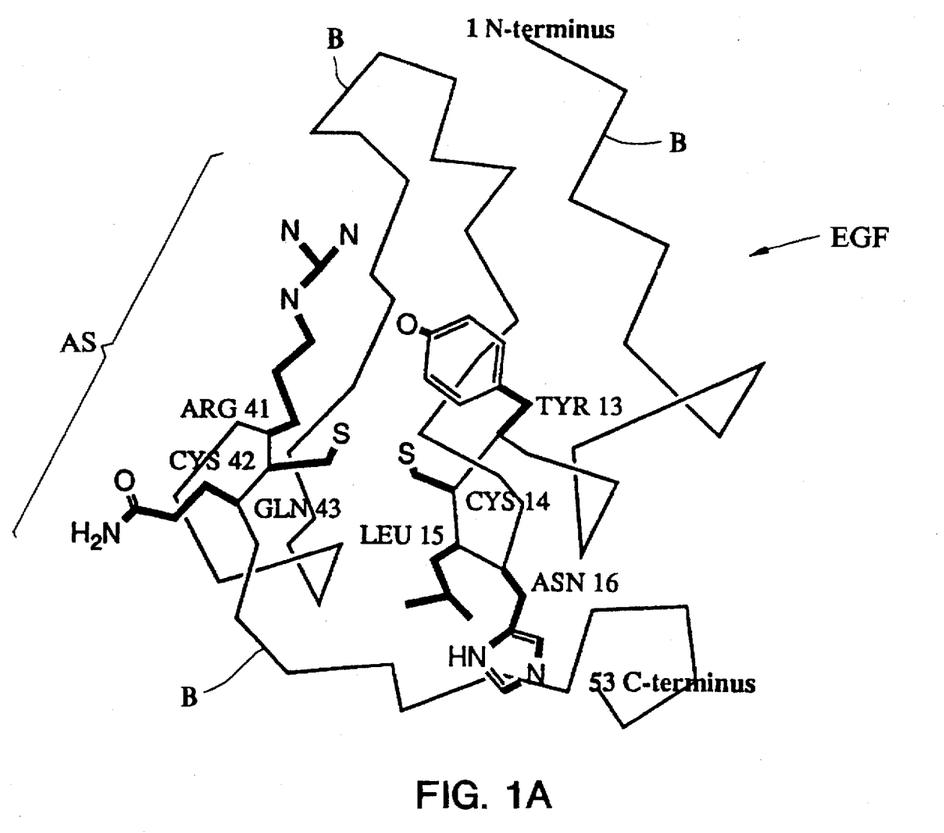
FIGS. 1a and 1b are representations of epidermal growth factor showing a putative active site.
Figure 1B:
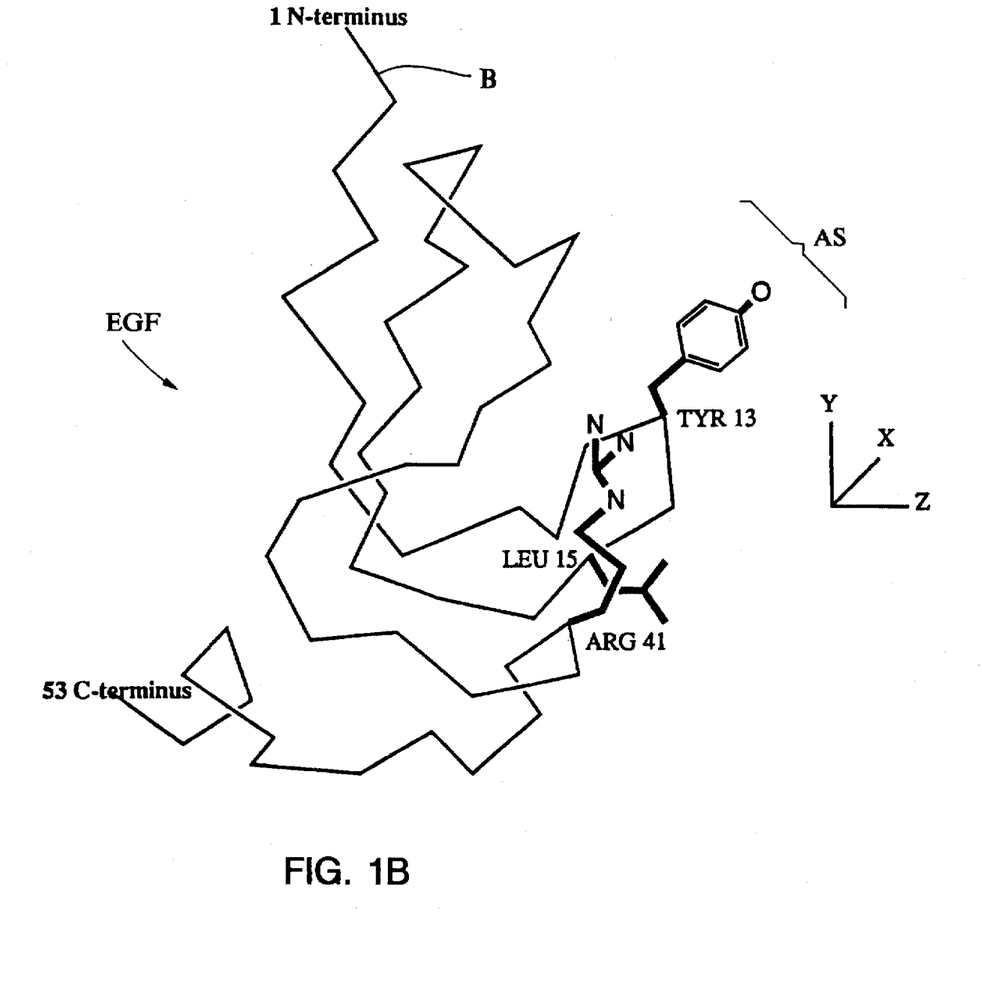

FIG. 1a is a representation of a protein, namely epidermal growth factor (EGF), showing its alpha carbon backbone B and the side chains TYR 13 (Tyrosine), CYS 14 (Cysteine), LEU 15 (Leucine), ASN 16 (Asparagine), and ARG 41 (Arginine), CYS 42 (Cysteine), and GLN 43 (Glutamine) of its putative active site AS. EGF has a complicated three-dimensional configuration, of which FIG. 1a is a two-dimensional projection. FIG. 1b is another projection of the molecule, rotated 90° around the Y-axis which is shown for reference in each of these two figures. (In FIG. 1b, for simplicity not all of the side chains of the putative active site AS are shown.)

Although the side chains TYR 13, LEU 15 and ARG 41, for example, are remote from one another in terms of distance along the alpha carbon backbone B, the projections of FIGS. 1a and 1b show that in three-dimensional space they are actually close to one another, and all three are part of the putative active site AS.

It is this active site AS which contributes to the particular biological activity of interest. An active site usually comprises several to many residues, or amino acids. These amino acids include the backbone atoms, which are linked together to form the polymer, and side chain atoms which protrude from the backbone. As illustrated by FIGS. 1a–1b, the amino acids which are members of the active site are not necessarily contiguous with one another. Thus, in determining what constitutes the active site AS, many amino acids may be selected which are remote from one another if one considers the path along the backbone B of the protein, but because of the folding of the molecule are brought physically close to one another in a well-defined configuration.

As discussed above, a primary goal of the present invention is to build artificial peptide chains which display essentially the same behavior as the active site. These peptide chains are considerably smaller and less complex than the naturally occurring protein, and directly connect residues which are remote from one another along the backbone, as described above.

Figure 5:
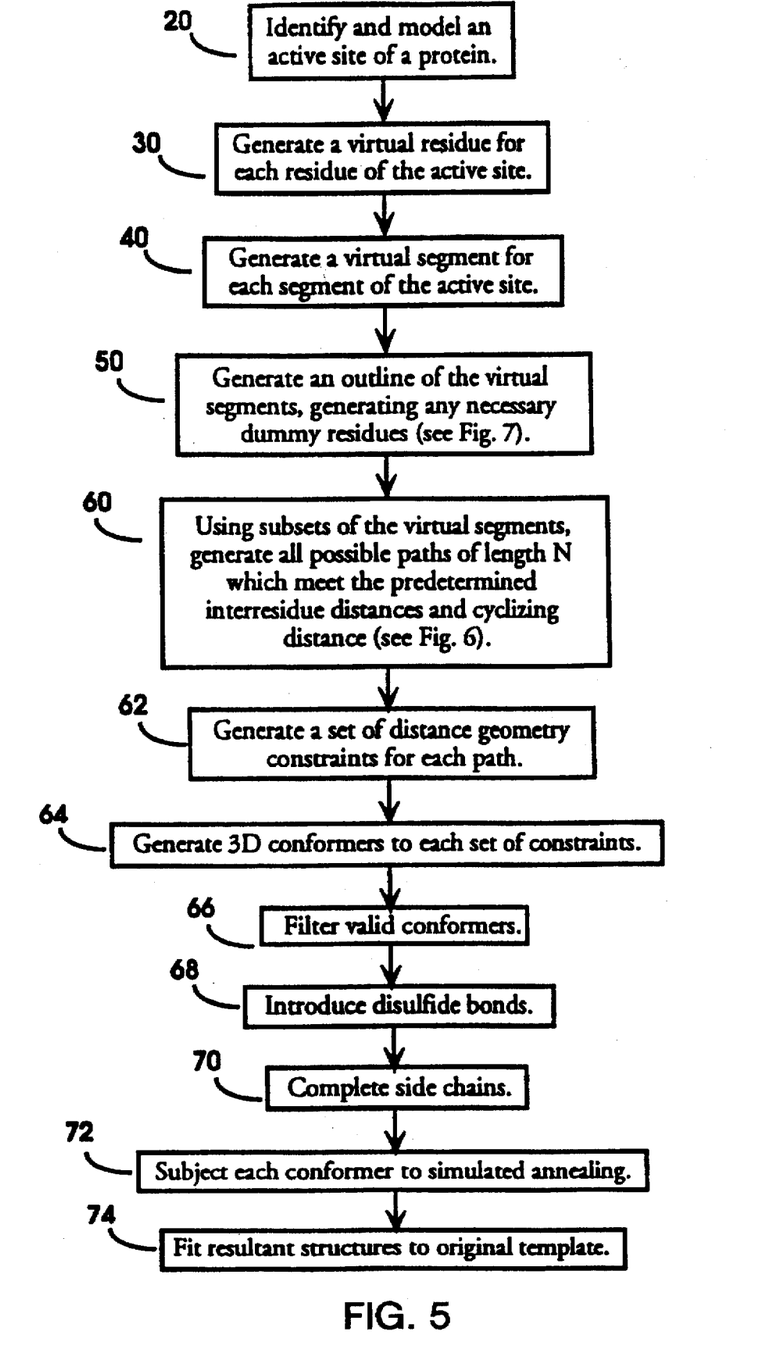
FIG. 5 is a flow chart of the basic method of the invention.

FIG. 5 is an overall flowchart for the method of the invention, each step of which is discussed in detail below. Beginning with step 20, the procedure is followed through step 70, at which point the user has generated a number of mimics of the active site of the protein of interest.

Step 20, identifying and modeling an active site of a protein, is carried out in a conventional manner known to biologists, particularly those familiar with protein chemistry computer modeling of molecules. See, for example: (1) E. P., Ripka et al., *Computer Graphics and Molecular Modeling in the Analysis of Synthetic Targets* in *Topics in Stereochemistry* 20, by E. L. Eliel et al. (Wiley, N.Y. 1991); (2) T. Gaetano et al., *Solution Structure of Murine Epidermal Growth Factor Determined by NMR Spectroscopy and Refined by Energy Minimization with Restraints*, Biochemistry, 1992, 31, pp. 236-249; (3) U. Hommel et al., *Structure-Function Relationships in Human Epidermal Growth Factor Studied by Site-Directed Mutagenesis and 1H-NMR*, Biochemistry, 1990, 30, pp. 8891-8898; and (4) E. Labriola-Tompkins et al., *Identification of the discontinuous binding site in human interleukin 1beta for the type 1 interleukin 1 receptor*, Proceedings of the National Academy of Sciences, USA, 88, pp. 11182-11186, December 1991. These references are incorporated herein by reference.

For the sake of example, the method herein is discussed in connection with epidermal growth factor (EGF). It is equally applicable to other proteins.

Figure 3:
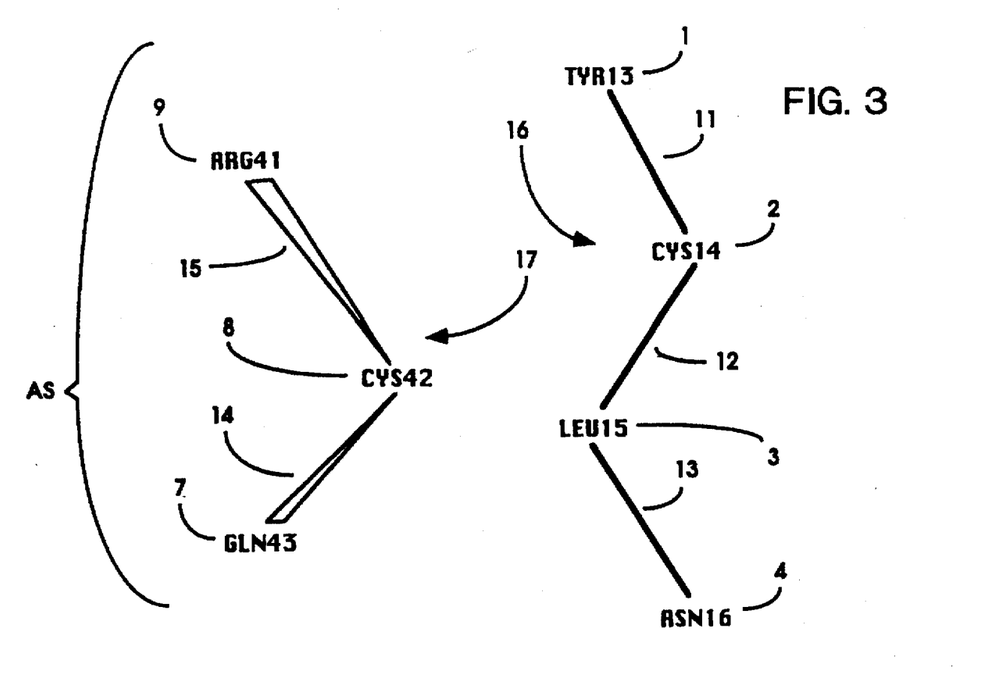
FIG. 3 is a representation of an active site of epidermal growth factor (EGF).

FIG. 3 shows a two-dimensional projection of the (actually three-dimensional) active site AS of EGF. The putative active site includes seven residues, namely: residue 1 (Tyrosine, or TYR 13); residue 2 (Cysteine, or CYS 14); residue 3 (Leucine, or LEU 15); residue 4 (Asparagine, or ASN 16); residue 5 (Glutamine, or GLN 43); residue 6 (Cysteine, or CYS 42); and residue 7 (Arginine, or ARG 41). In this active site, residues 1 and 2 (TYR 13 and CYS 14) are covalently bonded by bond 11; residues 2 and 3 (CYS 14 and LEU 15) are bonded by bond 12; and residues 3 and 4 (LEU 15 and ASN 16) are bonded by bond 13. Thus, residues 1–4 form a single segment 16 of amino acids which are actually attached in the original protein.

Residues 7, 8 and 9 are similarly contiguous and attached in the original protein by bonds 14 and 15, and thus make up the segment 17. Thus, the postulated active site AS of EGF in this case includes seven residues 1–7 in two segments 16 and 17.

As stated in step 30 of FIG. 5, each of the residues 1–7 is represented by a corresponding virtual residue in the memory 1020 of the computer 1000, in a manner which defines both the residue and its three-dimensional location. These representations are referred to together herein as the template of the active site. The template is stored in the memory 1020.

A virtual segment is represented in the memory 1020 for each actual segment 16 and 17, taking into account each of the bonds 11–15 of the actual protein. These computer-based representations are generated in a known manner, and include sufficient information to represent not only the positions of the residues, but also the bonding characteristics. Such representations of chemical structures are taught, for example, by J. McCammon et at., *Dynamics of proteins and nucleic acids*, Cambridge University Press (Cambridge 1989), which is incorporated herein by reference.

Initially, each of the residues and dummy residues is represented in memory as Alanine. As discussed below, this is changed once mimics are generated by the procedure of the invention.

Segments 16 and 17, and likewise residues 1–7, are accordingly called virtual segments and virtual residues, respectively, in the following discussion, when reference is made to the generation of the mimics. Whether the actual residues or segments or the virtual residues or segments is meant will be clear from the context.

As shown in FIG. 3, each of the residues in a given segment is connected to at least one other residue in that segment, and in this case to at most two other such residues. Depending upon the particular active site in question, it is also possible that a residue might be connected to only one other residue, forming a two-residue segment which constitutes the entire postulated active site. Another possibility is that a given residue may be connected to more than one other residue. The method as discussed below, while directed to the present example of the EGF active site, is equally applicable to such variations.

Once the virtual residues 1–7 and segments 15–16 are generated, an outline of the virtual segments is also generated, again taking into account the three-dimensional configuration, as well as the particular chemical bonds forming the actual segments. The segments and their residues as shown in FIG. 3 are thus completely represented in memory, as per step 40 of FIG. 5.

Pursuant to step 50 of FIG. 5, an outline 18 (shown in FIG. 4) is now generated, and is stored in memory. This outline comprises the segments 16 and 17 connected via dummy residues 5, 6 and 10, as shown.

Outline Generation Procedure

Figure 7:
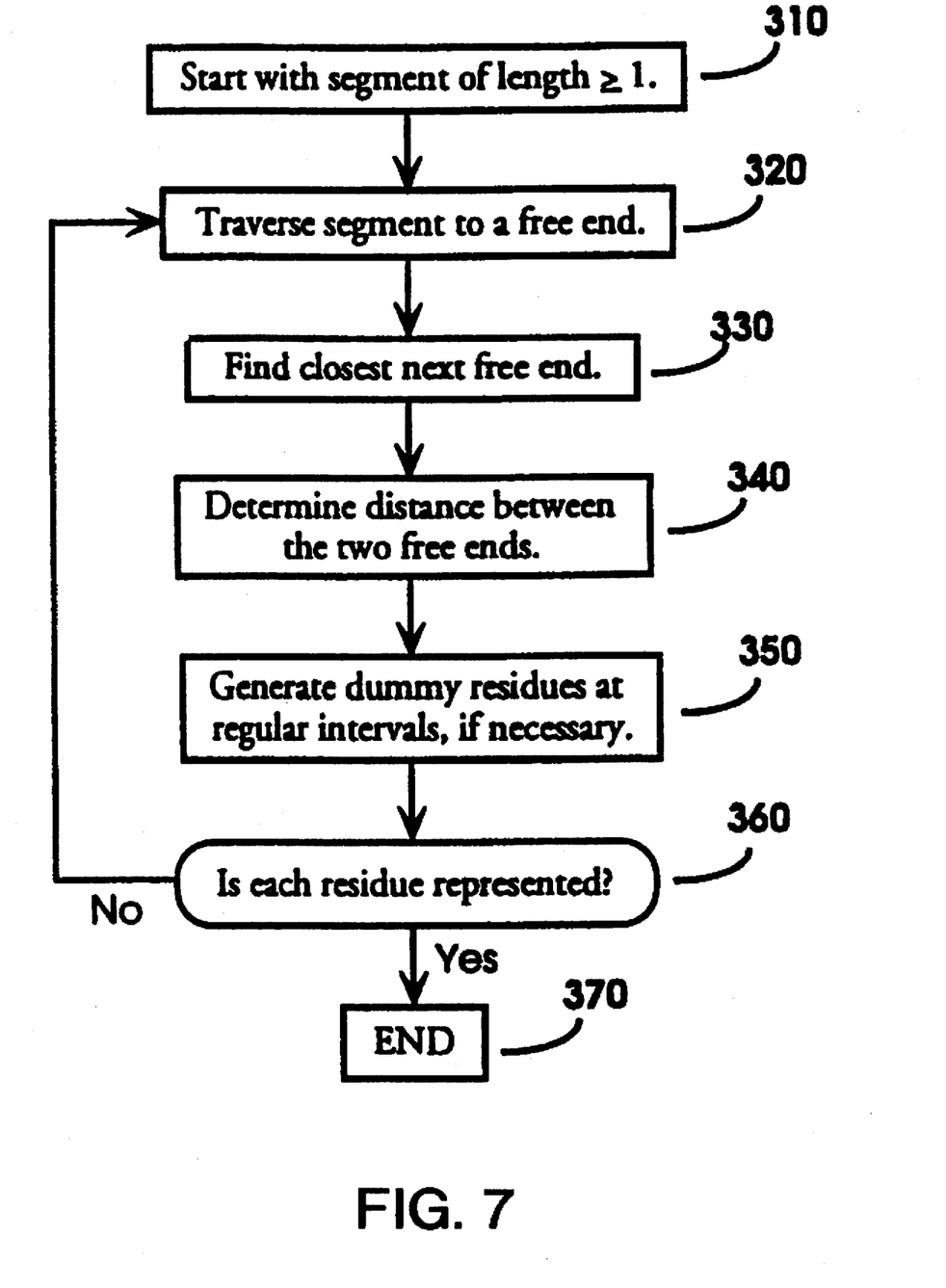
FIG. 7 is a flow chart depicting the procedure for generating an outline as in FIG. 4.

Step 50 is carried out in the outline generation procedure represented by the flow chart of FIG. 7. In step 310, the procedure starts with an arbitrary segment having a length of at least 1 (i.e., including at least one amino acid). In this example, the arbitrarily selected first segment is residue 1 (TYR 13).

Figure 4:
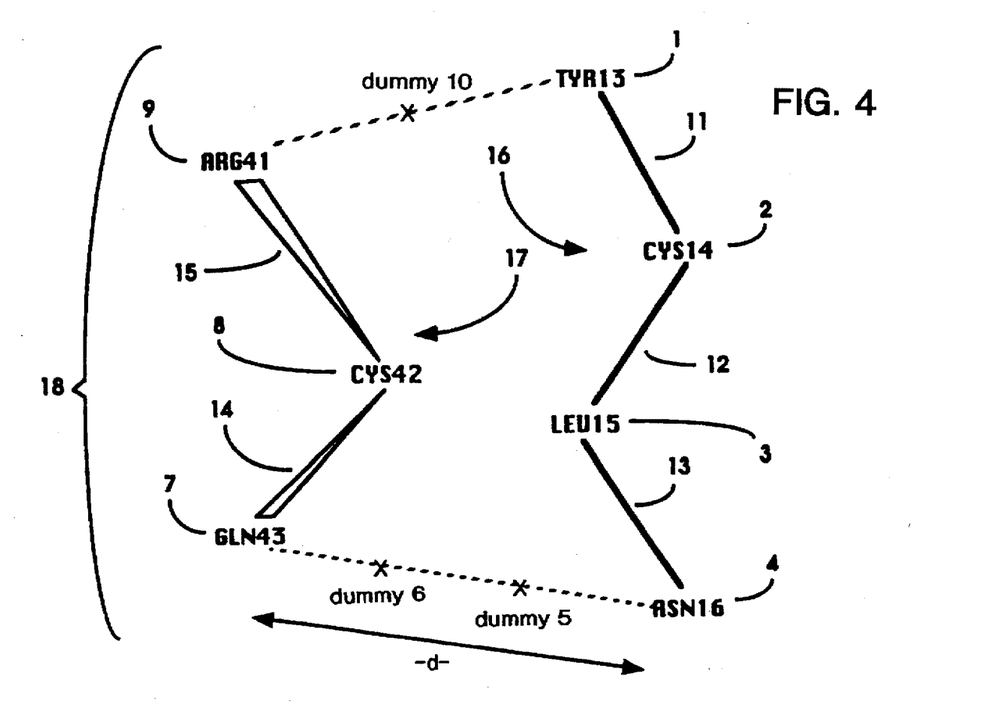
FIG. 4 is a diagram of an outline for generating mimics according to the invention, based upon the representation of FIG. 2.

Then, in step 320, the segment (here, segment 16) is traversed to an end, i.e. a place where an amino acid is unconnected on one end. In FIGS. 3–4, for example, such an end occurs at residue 4, which, in the actual EGF, is connected to only one other residue (residue 5). The residues 1–4 are already connected (both in the actual molecule and in the computer representation thereof), so that the procedure does not need to generate connections between these residues.

After traversing the segment 16 until the free end at residue 4 is reached, the closest free end of another segment is then located, as stated in step 330. In FIG. 4, the next free end after residue 4 is at residue 7.

In step 340, the distance d between the two free ends (see FIG. 4) is then determined. This is carried out in the processor by a standard three-dimensional geometrical calculation. If this distance d is less than or equal to a given predetermined distance D1, then the two free ends are directly connected in the computer's representation of the outline 18.

The distance D1 represents the maximum allowed interresidue distance, and is selected by the user based upon chemical considerations, such that in the mimic of the active site which is generated and which is ultimately synthesized in the laboratory, a proper covalent bond at the correct distance will be formed between the two free ends. In the present example, this distance D1 is 3.76 Å. A margin of error is also preferably provided, which in the present example will be 0.2 Å, such that the effective maximum interresidue distance is 3.96 Å. Other interresidue distances and margins of error (such as 4.0 Å) may be used, and will be somewhat within the discretion of the user, given the chemical constraints of the molecule.

If d>D1, then at least one dummy residue must be generated. (See step 350 of FIG. 7.) In the present example, then, at least one dummy residue must be generated between residues 4 and 7.

The actual number of dummy residues to be generated is equal to INT (d/D1), i.e. the integer part of the ratio of the interresidue distance divided by the maximum allowable interresidue distance. In the present example, the actual distance between ASN 14 and GLN 43 of EGF is 8.19 Å, and thus the number of residues is given by INT (8.19/3.96)=2. FIG. 4 therefore shows two dummy residues 5 and 6 between the residues 4 and 7.

In the EGF molecule, the distance between residues 9 and 1 (i.e. ARG 41 and TYR 13) is about 5.41 Å. Since INT (5.41/3.96)=1, a dummy residue 10 is also required between residues 9 and 1.

The above procedure is carried out until a complete, connected outline has been formed as in FIG. 4, with each residue represented in the outline (see step 360 of FIG. 7).

The dummy residues 5, 6 and 10 are positioned at substantially regular intervals between the respective virtual residues, and essentially on a straight line in three-dimensional space. If there is one dummy residue between two virtual residues, it is placed halfway between them, so that dummy residue 10 is about 2.7 Å from each of virtual residues 9 and 1. The dummy residues 5 and 6 are likewise evenly spaced at intervals of approximately 2.73 Å (since 8.19/3=2.73). In general, the spacing will be $d/(n+1)$, where d is the distance between the virtual residues to be connected and n is the number of dummy residues, determined as discussed above.

Figure 6:
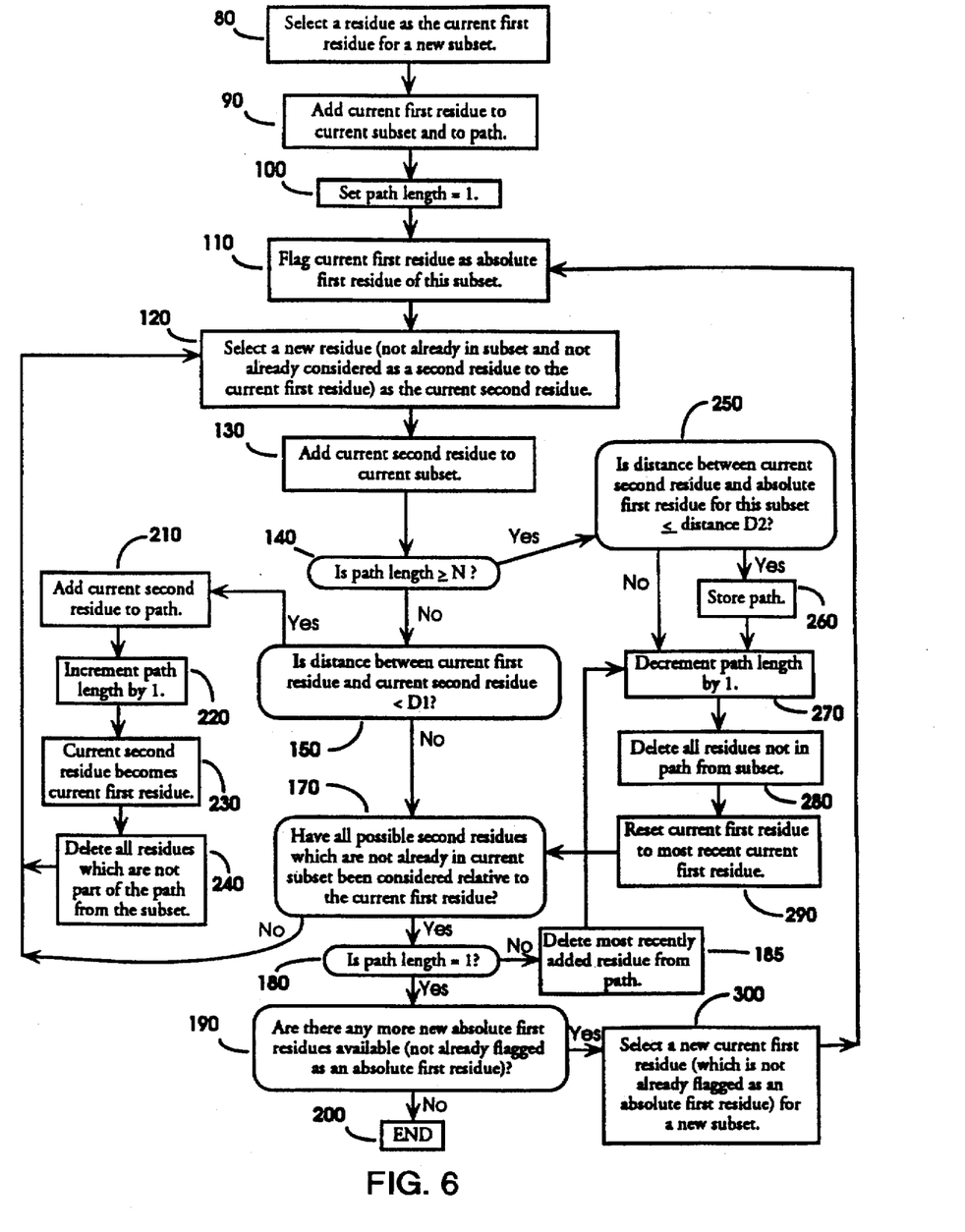
FIG. 6 is a detailed flow chart of the method of generating mimics of the active site of a protein.

The completed outline is now fully represented in memory, and can be used to generate mimics of the active site, as specified in step 60 of FIG. 5 and as set forth in detail in the flow chart of FIG. 6. This flow chart represents a recursive, depth-first search procedure, in which all paths of a predetermined length N are generated, based upon the outline of the active site. (Background on depth-first approaches may be found in *Applied Combinatorics* by Alan Tucker, John Wiley & Sons, New York, 1980.)

Generation of Paths: General Description

The generalized procedure of FIG. 6 is now discussed in connection with the specific outline example of FIG. 4.

The approach is basically to begin with a first residue, such as residue 1, and traverse the outline in all possible combinations, connecting the residues in different paths given the allowed interresidue distance D1 (here, 3.96 Å). There is one exception to the restriction that interresidue distances must not be greater than D1: the distance between the last residue in a given path back to the first residue, i.e. the distance for completing or "cyclizing" the path, may be allowed to be greater. In the present embodiment, this cyclization distance is referred to as distance D2 and is 6.32 Å.

The cyclization distance may be greater than the interresidue distances because of the various manners allowable in the present invention for cyclizing. These include: (1) regular peptide bond spacing (C-terminus to N-terminus), where D2 is 3.76 Å, with a preferable margin of error of ±2 Å; (2) Asparagine side-chain to N-terminus, where D2 is 3.96 Å to 4.4 Å; (3) disulfide closure, with both ends being Cysteines, where D2 is 4.4 Å to 4.7 Å; and (4) Glutamine side-chain to N-terminus, where D2 is 4.7 to 6.3 Å. Thus, setting D2 at 6.32 Å takes into account all of these possibilities.

The actual interresidue distances in the putative active site of EGF are given in the following table. These distances are stored in memory, and are used in a program implementing the invention.

TABLE 1

DISTANCE MATRIX BETWEEN ALPHA CARBONS IN EGF (in Å)

Alpha Carbon Number:

| | 1 | 2 | 3 | 4 | 5 | 6 | 7 | 8 | 9 | 10 |
|---|---|---|---|---|---|---|---|---|---|---|
| 1 | 0.00 | 3.86 | 7.01 | 10.18 | 9.34 | 9.26 | 9.96 | 8.38 | *5.41* | 2.70 |
| 2 | 3.86 | 0.00 | 3.78 | 6.41 | *5.78* | 6.36 | 7.91 | 5.51 | *4.38* | 3.12 |
| 3 | 7.01 | 3.78 | 0.00 | 3.85 | 2.94 | *4.16* | 6.40 | *4.98* | 5.73 | *5.81* |
| 4 | 10.18 | 6.41 | 3.85 | 0.00 | 2.73 | *5.46* | 8.19 | *6.09* | 8.53 | 8.99 |
| 5 | 9.34 | *5.78* | 2.94 | 2.73 | 0.00 | 2.73 | *5.46* | 3.83 | 6.50 | 7.58 |
| 6 | 9.26 | 6.36 | *4.16* | *5.46* | 2.73 | 0.00 | 2.73 | 2.67 | *5.16* | 6.99 |
| 7 | 9.96 | 7.91 | 6.40 | 8.19 | *5.46* | 2.73 | 0.00 | 3.81 | *5.09* | 7.43 |
| 8 | 8.38 | *4.98* | *4.98* | *6.09* | 3.83 | 2.67 | 3.81 | 0.00 | 3.86 | *5.93* |
| 9 | *5.41* | *4.38* | 5.73 | 8.53 | 6.50 | *5.16* | *5.09* | 3.86 | 0.00 | 2.70 |
| 10 | 2.70 | 3.12 | *5.81* | 8.99 | 7.58 | 6.99 | 7.43 | *5.93* | 2.70 | 0.00 |

Underlined distances are less than or equal to the maximum interresidue distance D1 = 3.96 Å, and are therefore allowed as either interresidue distances or as cyclization distances.
*Italicized distances* are less than or equal to the cyclization distance D2 = 6.32 Å, but greater than D1 = 3.96 Å, and are therefore allowed cyclization distances, but not allowed interresidue distances.
Plain-typeface distances are greater than D2 = 6.32 Å, and are not allowed distances for any part of a path.

The length of the paths to be generated (i.e. the total number of residues and dummy residues to be included in the cyclic path), based upon the outline 18 shown in FIG. 4, is preselected by the user, and may be governed by various considerations. For example, the longer the total path, the larger the molecule; and larger molecules in general have greater numbers of physical conformations which they can adopt, and hence less likelihood of being in the particular conformation required to fulfill the desired biological function. That is, the shorter the total allowed path length, and hence the smaller the molecule, the more determinate the conformation of that molecule will be, and therefore the more predictable its behavior.

On the other hand, the shorter the path length in a given mimic, the less specific its behavior will be, in the sense that there are fewer restrictions on the ways it can interact with other molecules; the smaller the number of residues, the smaller the number of criteria which have to be met for the molecule to interact. Thus, there is a balance to be struck in selecting the number of residues in the path for generating mimics.

In the current example, the path length N=7 is selected. This means that the total number of residues and dummy residues which will be represented in a given mimic of the outline of FIG. 4 will be seven. (The invention may be implemented using different path lengths which will generate various representations of the active site in question which may be compared for utility.)

Figure 8:
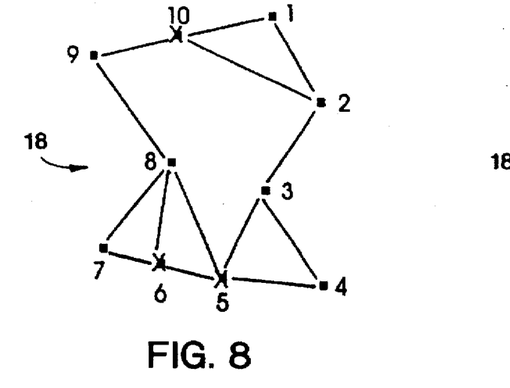
FIG. 8 is a representation of the outline of FIG. 4, showing allowed interresidue distances.

FIG. 8, which is a simplified representation of the outline of FIG. 4, provides a visual representation of which interresidue distances will be allowed, i.e. are less than the allowed interresidue distance D1 (3.96 Å). These allowed distances are represented by the line segments in FIG. 8.

Of course, any distance between consecutively numbered residues must be less than or equal to D1; this is how the outline 18 of FIG. 4 was constructed. Inspection of Table 1 above shows this to be the case: distance 1–2 (i.e. the distance between residues 1 and 2) is 3.86 Å, which is less than 3.96 Å; distance 2–3 is 3.78 Å; and so on.

In addition to the distances from 1 to 10 and back to 1, the following interresidue distances (which are underlined in Table 1) are allowed: 2–10; 3–5; 5–8; and 6–8. Each of these distances is thus represented by a line segment in FIG. 8.

D1 may also be subjected to a minimum test, below which a given interresidue distance will not be allowed. This alternative embodiment prevents the generation of mimics with residues which are so close to one another that the mimic molecule cannot properly be synthesized. In such an embodiment, a minimum value for D1 of 3.56 Å is preferable.

The italicized numerals in Table 1 are the distances which are allowed as cyclization distances. Thus, in addition to the allowed interresidue distances (which are, of course, also allowed cyclization distances), the following cyclization distances are allowed, i.e. are less than or equal to D2=6.32 Å: 1–9; 2–5; 2–8; 2–9; 3–6; 3–8; 3–9; 3–10; 4–6; 4–8; 5–7; 6–9; 7–9; and 8–9. These are graphically represented in FIG. 9.

Figure 9:
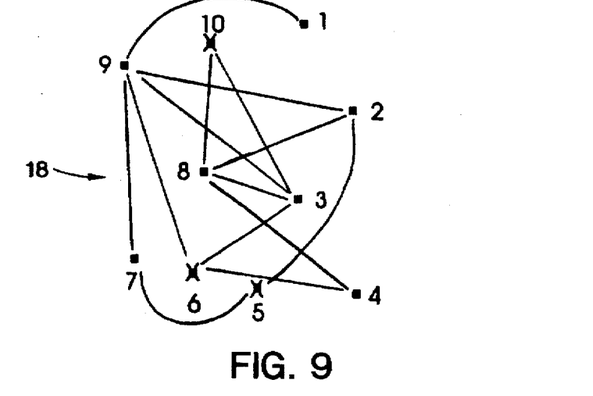
FIGS. 9–17 represent paths generated by the method of the invention.

A valid path constituting a mimic of the active site will comprise some combination of residues connected as shown in FIG. 8, with a single cyclization of the last-to-first residue according to one of the cyclization lines shown in FIG. 9. In addition, such a mimic will include N total residues.

Figure 10:
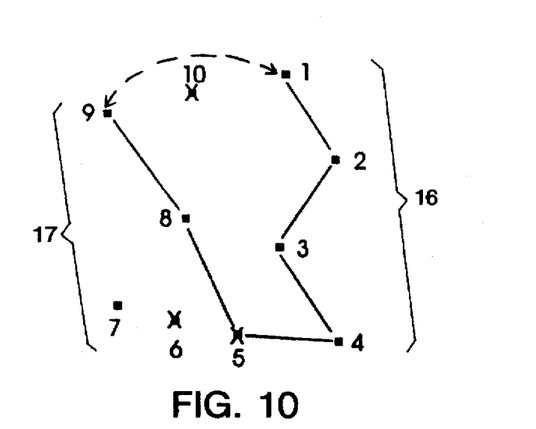

An example of a conforming path is shown in FIG. 10, wherein the solid lines represent allowed interresidue distances, while the dotted line is the cyclization distance between residues 9 and 1. In the path of FIG. 10, all of segment 16 is included, but only residues 8 and 9 are included from segment 17 (comprising residues 7, 8 and 9). Dummy residue 5 is also used, for a total of seven residues.

Figure 11:
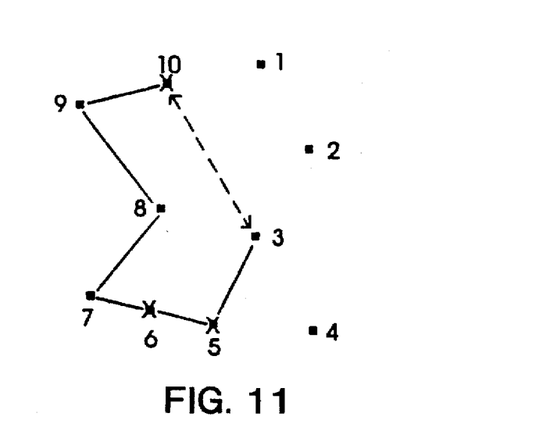

Another example of a conforming path is shown in FIG. 11, and includes all three dummy residues, only one residue from segment 16, and all the residues from segment 17. Again, since N=7, the total number of residues is seven.

Figure 12:
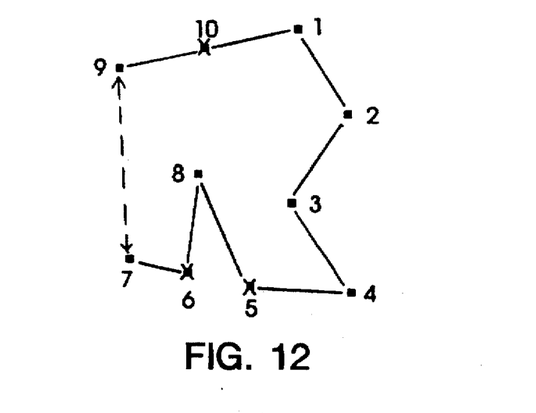
Figure 13:
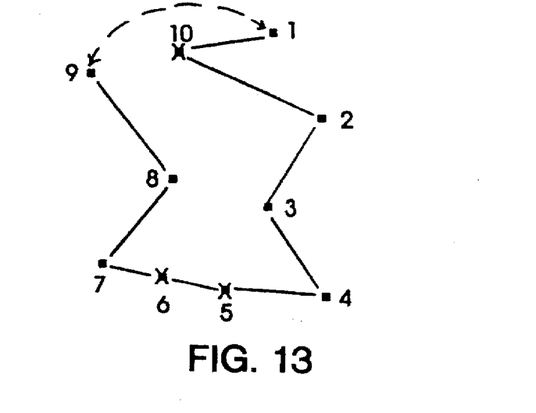

Of course, in the present example N=10 may be selected as the total number of residues, though it may in practice be difficult or impossible to the synthesize the mimic represented by the allowable paths; and even if it is synthesized, it may not, because of its size, conform reliably to the geometry of the actual active site. Note, however, that selecting N=10 does not restrict one to connecting the residues as in the outline 18 of FIG. 4; because the cyclization distance is greater than the allowable interresidue distance, there is flexibility in the paths which may be chosen. Thus, either of the paths shown in FIGS. 12 and 13 would be proper for a path length of N=10.

As stated in step 60 of the flow chart of FIG. 5, for a given value of N the method generates all possible paths which meet the distance criteria. The following table shows the number of possible paths for various values of N, with ten amino acids represented in an outline for EGF, with D1=3.96 Å and D2=6.32 Å:

TABLE 2

| N | Number of possible paths |
|---|---|
| 5 | 85 |
| 6 | 105 |
| 7 | 149 |
| 8 | 173 |
| 9 | 109 |
| 10 | 33 |

Note that N cannot be more than ten, since each residue may be connected, in the embodiment under discussion, to only two other residues. If N were eleven, then at least one residue would have to be used redundantly, i.e. connected to more than two other residues.

If there were no distance constraints, the total number of possible paths of length N with ten total residues would be $P(10,N)=10!/(10-N)!$. For N=7, without distance constraints there would be 3,628,800/6=604,800 possible paths. However, given the distance constraints mentioned above, for a value of N=7, there are only 149 total possible paths in the present example.

Generation of Paths: Detailed Implementation

These paths are generated by the method represented in FIG. 6. In step 80, a residue is selected as the first residue; at this point, residue 1 may be selected. This is at present the "current first residue", i.e. the residue with respect to which the next residue is selected and inspected for the correct interresidue distance.

In step 90, residue 1 is added to the current subset, which is a subset of the total set of residues. The subset is stored in memory, and represents all of the residues which have been considered at a given point as possible members of the path being generated. Thus, at this point, the subset contains exactly one residue, namely residue 1. Residue 1 is also added to the path generated to this point, which is also stored in memory.

At step 100, a path length variable is initialized to one. Then, at step 110, residue 1 is flagged as being the "absolute" first residue of the current subset. Thus, residue 1 is at this point both the absolute first residue and the current first residue.

At step 120, a new residue is selected, in this case residue 2, as the current second residue, and at step 130 it is added to the current subset. At step 135, the path length is incremented to 2.

At step 140, it is determined whether the path length is at least N. If not (as in the present case), then in step 150 the distance between the current first and second residues, i.e. residues 1 and 2, is compared to D1. Here, the residue 1-2 distance is 3.86 Å, which is less than D1=3.96 Å so we proceed to step 210, and residue 2 is added to the path.

At step 230, residue 2 becomes the current first residue, and at step 240, any residues which are not part of the path are deleted from the subset. (At this point, there are no such residues.)

Proceeding back to step 120, residue 3 is now selected. Since it is less than 3.96 Å from residue 2, it is also added to the path at step 210. The method proceeds until, in this example, residues 1–6 have all been added to the path. Branching back to step 120, after the addition of residue 6 in step 210, residue 7 may now be added to the path.

Figure 14:
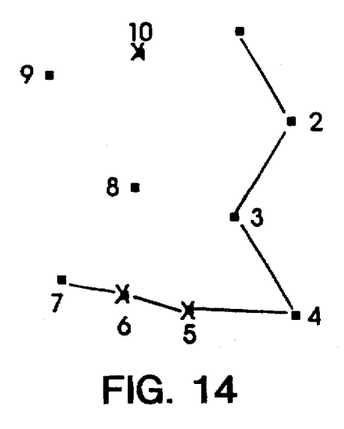

At step 120, residue 7 becomes the current first residue, and the path at this time has the configuration shown in FIG. 14. Residue 8 becomes the current second residue and is added to the subset. However, at step 140, it is found that the path length (presently 7) is equal to N, so the method proceeds to step 250.

At step 250, the residue 7-residue 1 distance is compared to D2; the former is 9.96 Å, and the latter is 6.32 Å, so the method proceeds to step 270. The path length now again equals six, and at step 280, residues 7 and 8 are deleted from the subset.

At step 290, residue 7 is reset as the current first residue. At step 170, it is determined whether there are any other possible second residues relative to current first residue 7 which have not already been considered (and are not already part of the subset). This leaves residues 9 and 10. However, the results are the same for these residues, because the path is already seven residues long.

Thus, the configuration of FIG. 14 does not lead to a valid path; the cyclization cannot be completed from residue 7 to residue 1, and no additional (closer) residues can be added, since the path length already stands at N=7.

When step 170 is again reached, the result is "Yes", and the method proceeds to step 180. Since the path length does not equal 1, residue 7 is deleted from the path (step 185), and the path length is decremented (step 270).

At step 280, residue 7 is removed from the subset, and at step 290, residue 6 is reset to the current first residue. It will soon be found, following through the steps, that residue 8 is also not a valid next residue relative to residue 6, since cyclization is not possible from residue 8 to residue 1 (and no more residues can be added, or the path length would exceed seven). The distances from residue 6 to residues 9 and 10 are too great, so this path (so far consisting of 1–6) is a dead end.

The method then backs off one more residue, deleting residue 6 at step 185 just as residue 7 was previously deleted. Proceeding to step 270, the path length is decremented to five, and residue 6 is deleted from the subset. At step 290, residue 5 is set to become the current first residue.

The answer to the test in step 170 is "No", so the method proceeds via step 240 to step 120. Residue 7 is initially selected as the current second residue, but the distance (5.46 Å, from Table 1) is found to be too great, so residue 7 fails the test of step 150, and the method proceeds around again to step 120 (via steps 160 and 170).

Now, residue 5 is again set to the current first residue, and residue 8 is selected as the current second residue. Referring to Table 1 (and FIG. 8), it is found that the residue 5-residue 8 distance (3.83 Å) is less than D1, so residue 8 is added to the path at step 210, and the path length is incremented to six.

Proceeding around again to step 120, residue 9 is considered, found to be within distance D1, and is added to the path at step 210. The path length is incremented to seven at step 220.

At step 230, residue 9 becomes the current first residue. At step 120, residue 10 is selected as the current second residue, and at step 130 it is added to the subset.

At step 140, it is found that the path length equals N (i.e., seven), so the method branches to step 250, where it is found that the residue 9-residue 1 distance (5.41 Å) is less than D2 (6.32 Å). Thus, this is an allowable cyclization distance, and at step 260 the path 1-2-3-4-5-8-9-1 is stored.

This is the first cyclized path located by the method, assuming the residues are considered in ascending numerical order as discussed above. The resulting path is represented in FIG. 10.

Figure 15:
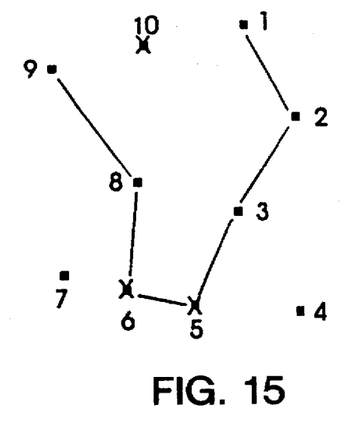

It will readily be seen that the next valid path generated by the above method is that shown in FIG. 15. Referring to FIG. 8, it is clear that no other paths are available which include 1-2-3-4-5, and none are available involving 1-2-3-4 except with residue 5 as the next residue.

Thus, the method backs up to a path of 1-2-3, then locates 5-6-7-8 (for a path of 1-2-3-5-6-7-8), but finds that cyclization from residue 8 to residue 1 is not possible. The path again backs up to 1-2-3-5-6, adds residue 8, and then residue 9, and then cyclizes to residue 1. The resulting path is that of FIG. 15, namely 1-2-3-5-6-8-9-1.

Once all the possible paths beginning with residue 1 have been considered, the answer to step 180 becomes "Yes", and the method branches to step 190. Since residues 2–10 have not yet been flagged as absolute first residues (see step 190), residue 2 is selected in step 300 as the new current first residue. In step 110, it is flagged as an absolute first residue, and the process begins again, but this time with residue 2 as the first residue of the subset.

Figure 16:
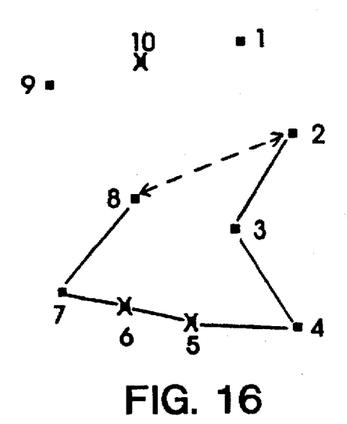
Figure 17:
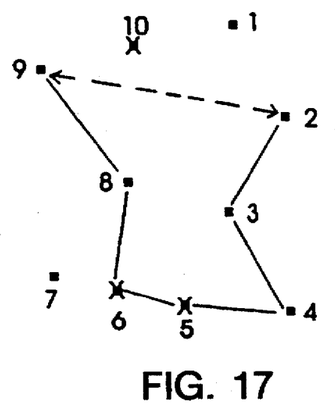

The first valid path (which is stored at step 260) using residue 2 as the first residue is 2-3-4-5-6-7-8-2, shown in FIG. 16. The second valid path which is found is 2-3-4-5-6-8-9-2, which is shown in FIG. 17.

Residues 3–10 are each, in turn, considered as the absolute first residue of the current subset. The procedure thus methodically generates, in a depth-first search, all possible paths which meet the length and distance criteria, and stores them. Other searches, such as a breadth-first search, might also be applied to the present method without altering the basic nature of the invention. However, the depth-first search makes for an efficient implementation.

The Interresidue Bonds

Figure 18:
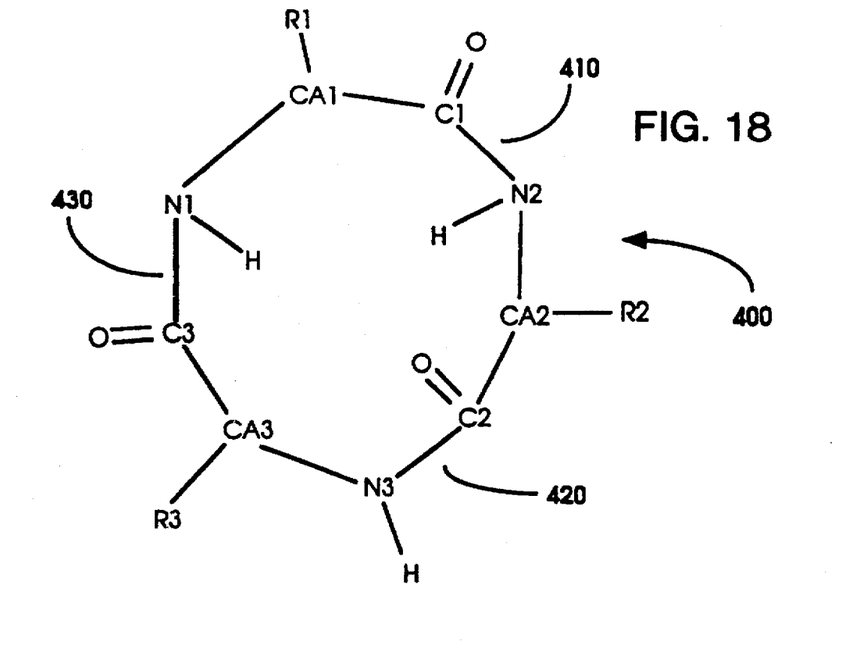
FIG. 18 is a simplified representation of a mimic similar to those generated by the invention.

It will be clear to those familiar with protein structures that the connections between residues in the mimics generated as described above are generally to be made as carbon-nitrogen (CN) bonds. As a simplified example, FIG. 18 shows a three-residue structure, thus having a total of three alpha carbons CA1, CA2, and CA3 (as well as three carbonyl carbons C1, C2 and C3). The bonds between the respective residues are: bond 410 (between C1 and N2); bond 420 (between C2 and N3); and bond 430 (between C3 and N1).

In this example, the suffix "1" denotes the first residue, "2" denotes the second residue, and "3" denotes the third residue. Thus, the cyclization bond is bond 430, between C3 of the third residue in the path and N1 of the first residue.

It is also possible, however, that the cyclization bond could be formed between the side chain R3 and N1, in which case the side chain must include a CO group, since the bond is always between a CO group and an N. Thus, where an amino acid has a side chain R which comprises a CO group, this side chain may be available for the interresidue bonds. Such is the case, for example, with Aspartic acid and Glutamic acid. Other cyclization variations are possible, as discussed above.

Note that a given path is not, in general, identical to the reverse thereof. Thus, a path of 1-2-3-5-6-8-9-1 will result in molecule which, in general, is physically different from 1-9-8-6-5-3-2-1, because of the asymmetries resulting from the interresidue bonds described above.

Distance Geometry

Although the paths discussed above were generated based upon the actual three-dimensional geometry of the active site, this is not sufficient to ensure that the resultant proposed structures can exist in three-dimensional space. Because of the complicated nature of the positions and angles between the residues, it is necessary to test whether the generated paths are valid. This type of problem is dealt with, for instance, in (1) G. M. Crippen, *Distance Geometry and Conformational Calculations*, Research Studies Press (Wiley, N.Y. 1981); and (2) G. M. Crippen et al., *Distance Geometry and Molecular Conformation*, Research Studies Press (Wiley, N.Y. 1988). A program called "DGEOM" has been written for solving such geometrical problems as the above, by J. Blaney et al., and is referenced as "DGEOM", #590, Quantum Chemistry Program Exchange, Indiana University: Bloomington, 1990. (The documentation accompanying the program describes it in detail.) Each of the foregoing references is incorporated herein by reference.

Thus, in step 62 of FIG. 5, a set of distance geometry constraints is generated for each of the successful paths. In so doing, chirality is allowed to vary randomly (D or L) at each residue. Then, in step 64, a conforming structure is generated based upon each set of constraints. For each set of constraints, a number n of three-dimensional structures are generated, where n may be selected to be a reasonably small, such as 5.

The resultant structures comprise three-dimensional coordinates for all of the atoms in the cyclized peptides. However, because of the constraints placed on the poly-Alanine by linking residues together, some of the paths do not lead to successful three-dimensional conformers. Thus, in step 66, the valid conformers are filtered, i.e. only the successful conformers are selected.

By way of example, in a particular test run of the method of the invention, the following results were achieved. Table 3 represents the same data as Table 2, with the addition of the third column, showing the number of generated paths which were actually three-dimensionally possible:

TABLE 3

| N | Number of possible paths | Number of possible 3D Structures |
|---|---|---|
| 5 | 85 | 72 |
| 6 | 105 | 82 |
| 7 | 149 | 112 |
| 8 | 173 | 134 |
| 9 | 109 | 89 |
| 10 | 33 | 27 |

Thus, in practice it can be seen that considerable effort is spared by rejecting at this point the generated paths which are not capable of actual synthesis.

Disulfide Bonds

In order to contribute to the rigidity of a molecule which is ultimately synthesized, it is helpful to make it bicyclic, i.e. having two cycles. This is accomplished in step 68 of FIG. 5 by introducing disulfide bonds between two residues of the mimic. Disulfide bonds are a common means of stabilizing peptides, and most naturally occurring proteins have one or more.

Figure 19:
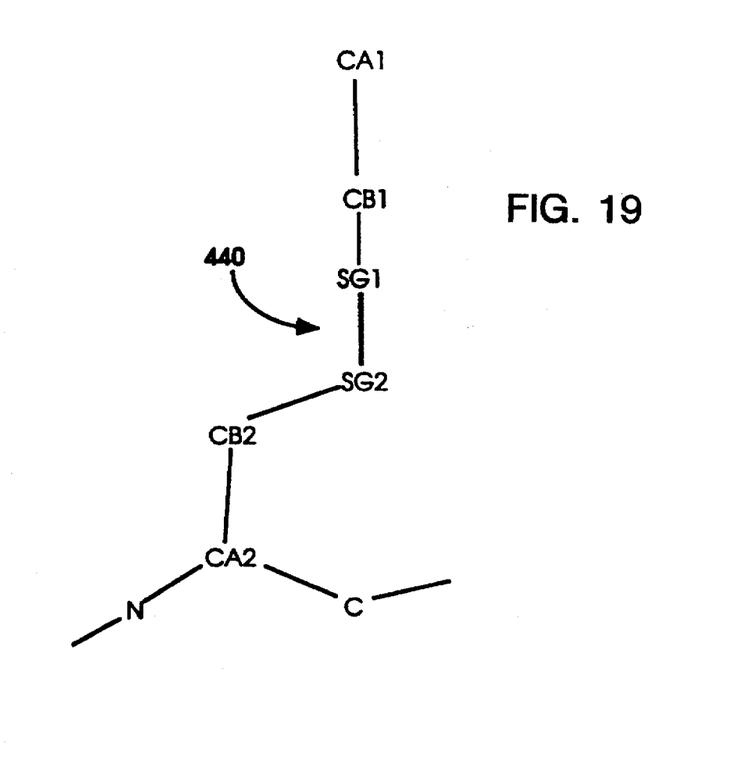
FIG. 19 is a representation of a portion of a molecule, showing the disulfide bond.

FIG. 19 shows a representation of a portion of two residues or a molecule, having alpha carbons CA1 and CA2, respectively, as well as beta carbons CB1 and CB2 and gamma sulfurs SG1 and SG2. The disulfide bond 440 is between the two sulfurs, which are in turn attached to the respective beta carbons. The residues having the sulfur side chains are Cystines, and are substituted for the residues which would otherwise be present at those points.

The disulfide distances for bonding are important to govern carefully. Since at this stage we have only a poly-Alanine chain, alpha-carbon positions and beta-carbon positions are defined, but not, as yet, sulfur positions. The incorporation of a disulfide bond between two hypothetical sulfurs (in Cysteines) is based upon the distances between the respective alpha- and beta-carbons of two residues. From minimized structures of known disulfides, we have derived minimum and maximum alpha carbon-alpha carbon and beta carbon-beta carbon distances, as follows:

Minimum CA—CA distance: 4.6 Å

Maximum CA—CA distance: 7.4 Å

Minimum CB—CB distance: 3.6 Å

Maximum CB—CB distance: 4.0 Å

Allowed margin of error in each of the above: 1.0 Å

The above values are exemplary only, and other values may be selected or derived.

Thus, the method of the invention generates at least one disulfide for each of the valid paths, and this is represented in the computer model of the path for generating the mimic. This may be done by replacing the appropriate dummy residue(s) in the mimic with Cysteine, so that active site residues are not displaced. More than one disulfide bond may be used in a given mimic.

Side Chains

In step 70 of FIG. 5, the side chains are added to the residues, which until now have been represented as Alanine (except for the Cystines in the case of the disulfide bonds). This representation must be changed by adding side chains to all but the dummy residues. The side chains correct the stored representations of the residues to bring them into agreement with the actual residues, such as those in the outline 18 shown in FIG. 4.

The dummy residues are best left as Alanine. When a mimic is actually synthesized, it is best that the dummy residues have as lit fie biological effect as possible. Alanine is relatively simple and small, and it has no hydrophilic groups; rather, the single side carbon is somewhat hydrophobic. As a result, Alanine is easily "buried" in the resulting molecule, and is less likely to interfere with the reactions of the "real" residues, i.e. those actually representing amino acids found at the active site of the protein.

Note that Alanine is a component of almost all other amino acids. For this reason, simply adding the appropriate side chain atoms in the representation of the paths converts them to the appropriate amino acids. The only exception to this is in the case of Glycine, which has a hydrogen in the place of Alanine's beta carbon. If a Glycine is needed at a particular residue site, it may be substituted at this point.

It is a straightforward matter to add on the side chains in the models of the valid conformers, given the known structure of the active site.

Simulated Annealing

The different mimics of which complete models are now stored, including disulfide bonds and side chains, are subjected to simulated annealing, as stated at step 72 of FIG. 5. This involves modeling in the processor the gradual heating and then cooling of the represented molecules, and locates local or perhaps even global energy minima for the molecules. The results in stabilizing the molecule by tending to bring it into its lowest available energy state. A program called CHARRM and its accompanying documentation, commercially available from Polygen Corporation of Waltham, Mass., is useful for this step, and is incorporated herein by reference.

The simulated annealing is carried out in a very straightforward manner, by calculating the trajectories of each individual atom in a given molecule on, preferably, a femtosecond-by-femtosecond basis, using a classical dynamics model and taking into account, among other things: (1) the energy structure of the bond; (2) the bending of bond angles; (3) the rotation of bonds; and (4) the repositioning of atoms.

To make the simulated annealing more accurate, it is preferable also to insert water molecules (500–1000 for a given simulation) into the modeled system.

When the simulated annealing is complete, the user has available a set of completely defined, stabilized mimics of various configurations which represent the active site or portions thereof. These mimics are virtual; i.e. they have not actually been made, but only generated in principle. In practice, one would then actually synthesize these molecules to test their efficacy as substitutes for the original subject protein. Those skilled in the art will be able to select appropriate virtual mimics generated by the invention to be realized in the laboratory. This is done by well-known techniques of molecular synthesis, as taught, for instance, in the following articles, which are incorporated herein by reference: A. M. Gray et al., *J. Org. Chem.* (1991) 56: 6659–66; R. M. Valerio et al., *Anal. Biochem.* (1991) 197: 168–77, and H. M. Geysen et al., *J. Immunol. Meth.* (1987) 102: 259–74.

We claim:

1. A method for generating mimics of a predetermined active site of a protein, said active site having a known three-dimensional configuration of a plurality of residues, the method being executed by a computer having a microprocessor coupled to a memory and utilizing a program including program steps implementing the method, the method including the steps of:

(1) generating and storing in memory a virtual residue corresponding to each of the residues of the active site, each said virtual residue having a defined position which corresponds to a physical location of the corresponding residue of the active site;

(2) generating and storing in memory a virtual segment corresponding to each segment of the active site, a segment being a group of at least one residue, wherein all of the residues of a given segment are connected;

(3) (a) when step (2) provides a plurality of virtual segments, generating and storing in memory an outline of said virtual segments having defined positions which correspond to physical locations of corresponding actual segments of the active site;

(b) when step (2) provides only a single virtual segment and said virtual segment has two free ends, generating and storing in memory an outline of said virtual segment having defined positions which correspond to physical locations of corresponding actual segment of the active site;

(c) when step (2) provides only a single virtual segment and said virtual segment has fewer than two free ends said virtual segment defines an outline of said virtual segment having defined positions which correspond to physical locations of corresponding actual segment of the active site;

(4) generating an storing in the memory of at least one path of the active site including a first subset of said virtual segments represented in the outline; and (5) mapping the path onto the corresponding residues in the active site, thereby generating the mimic of the site, and storing said mimic in the memory.

2. The method of claim 1, wherein step 2 includes the steps of:

(6) determining, for a first said virtual residue, whether the actual residue which it represents is connected to at least one other residue in said active site;

(7) if the determination in step 6 is positive, then linking said first virtual residue to the virtual residue corresponding to said one other residue; and (8) repeating steps 6 and 7 for each of the residues of the active site, thus generating a plurality of virtual segments, where each virtual segment includes at least one virtual residue, the virtual residues having a one-to-one correlation to residues in connected segments in the active site.

3. The method of claim 1, wherein step 3 includes the steps of:
(9) defining for each virtual segment a first end and a second end which correspond to ends of the actual segment to which each said virtual segment corresponds;
(10) locating, for the second end of a first virtual segment, the first end of a second virtual segment which is closest to it;
(11) linking said second end of said first virtual segment to said first end of said second virtual segment; and
(12) repeating steps 10 and 11 for the second and third virtual segments, and then for each successive pair of virtual segments, until each virtual segment is connected at its first end to the second end of a preceding virtual segment and at its second end to the first end of a succeeding virtual segment.

4. The method of claim 3, further including the steps of:
(13) in step 10, determining whether a gap between said first end of the second virtual segment and the second end of the first virtual segment is greater than a predefined maximum distance;
(14) if the determination of step 13 is positive, then inserting at least one dummy residue between and linked to said first end and said second end; and
(15) repeating steps 13 and 14 for each of the successive pairs of residues for which steps 10 and 11 are carried out in step 12.

5. The method of claim 4, wherein the number of dummy residues in step 14 is determined by taking the integer part of the ratio of the gap to the predefined maximum distance.

6. The method of claim 5, wherein, if said integer part is one, then the dummy residue is inserted at a point substantially equidistant from the second end of the preceding segment and the first end of the succeeding residue.

7. The method of claim 5, wherein, if said integer part is greater than one, the residues are substantially equally spaced between the second end of the preceding segment and the first end of the succeeding residue.

8. The method of claim 1, wherein step 4 includes the step of:
(16) generating a plurality of paths of the active site, wherein one such path is generated for each of a plurality of subsets of virtual residues wherein the distance between any two linked virtual residues is less than a predefined maximum distance, and wherein one said mimic is generated for each said path.

9. The method of claim 8, wherein step 16 comprises generating a plurality of said subsets, including the steps of:
(17) selecting a virtual residue of said outline as the current first residue of a current subset;
(18) generating a residue path beginning with said current first residue;
(19) setting a path length variable equal to zero;
(20) flagging the current first residue as the absolute first residue of the current subset;
(21) selecting as the current second residue another virtual residue of said outline which does not yet form a part of the subset and which has not previously been selected as a second residue relative to the current first residue;
(22) adding the current second residue to the current subset;
(23) incrementing the path length variable by one;
(24) determining whether the path length variable is greater than a predetermined maximum path length, and if not, proceeding to step 30;
(25) determining whether the distance between the current second residue and the absolute first residue for this subset is less than a predetermined maximum cyclization distance D2, and if not, proceeding to step 27;
(26) storing the path;
(27) decrementing the path length variable by one;
(28) deleting all the residues which do not form a part of the path from the current subset;
(29) selecting the immediately preceding current first residue as the current first residue, and proceeding to step 34;
(30) determining whether the distance between the current first residue and the current second residue is less than or equal to a predetermined maximum interresidue distance D1, and if not, proceeding to step 33;
(31) adding the current second residue to the path;
(32) selecting the current second residue as the current first residue;
(32a) deleting all residues which do not form a part of the path from the subset, and proceeding to step 21;
(33) decrementing the path length variable by one;
(34) determining whether all possible second residues not already in the current subset have been considered relative to the current first residue, and if not, proceeding to step 32a;
(35) determining whether the path length variable is equal to zero, and if not, proceeding to step 27;
(36) determining whether there are any more new absolute first residues available, and if not, proceeding to step 38;
(37) selecting a new current first residue, which has not yet been flagged as an absolute first residue, for a new subset, and proceeding to step 20; and
(38) ending the subset generating procedure, whereby said stored paths constitute said generated plurality of paths of the active site.

10. The method of claim 9, wherein the distance D2 is greater than the distance D1.

11. The method of claim 8, wherein step 16 includes the step of limiting the length of each path to a predetermined maximum.

12. The method of claim 1, including, after step 3 and before step 4, the step of determining whether the path can be mapped onto three-dimensional space.

13. The method of claim 1, including, after step 5, the step of generating physical constraints for a polypeptide corresponding to the path.

14. The method of claim 1, including, after step 5, the step of generating a stabilizing bond between two nonadjacent residues in the path.

15. The method of claim 1, including, after step 5, the step of optimizing the mimic by simulated energy minimization.

16. The method of claim 1, further including the step of synthesizing a molecule based upon the generated mimic of the active site.

17. The method of claim 1, wherein each virtual segment is linked in said outline to at least one other virtual segment.

18. The method of claim 1, wherein each virtual segment is linked in said outline to exactly two other virtual segments.

19. The method of claim 1, wherein at least one virtual segment is linked in said outline to more than two other virtual segments.

* * * * *